(12) United States Patent
Campin et al.

(10) Patent No.: US 9,931,515 B2
(45) Date of Patent: Apr. 3, 2018

(54) POWERED CASE FOR ELECTRO-ACTIVE MEDICAL DEVICE BATTERY MANAGEMENT

(71) Applicant: Novartis AG, Basel (CH)

(72) Inventors: John Alfred Campin, Southlake, TX (US); Michael F. Mattes, Arlington, TX (US)

(73) Assignee: Novartis AG, Basel (CH)

( * ) Notice: Subject to any disclaimer, the term of this patent is extended or adjusted under 35 U.S.C. 154(b) by 252 days.

(21) Appl. No.: 14/973,214

(22) Filed: Dec. 17, 2015

(65) Prior Publication Data

US 2017/0173344 A1    Jun. 22, 2017

(51) Int. Cl.
| | | |
|---|---|---|
| G01R 1/20 | (2006.01) | |
| A61N 1/378 | (2006.01) | |
| A61B 5/00 | (2006.01) | |
| A61F 2/16 | (2006.01) | |
| A61M 5/142 | (2006.01) | |
| H02J 7/00 | (2006.01) | |
| A61N 1/39 | (2006.01) | |
| H02J 7/02 | (2016.01) | |

(52) U.S. Cl.
CPC .......... *A61N 1/3787* (2013.01); *A61B 5/6846* (2013.01); *A61F 2/1613* (2013.01); *A61M 5/142* (2013.01); *A61N 1/3931* (2013.01); *A61N 1/3968* (2013.01); *A61N 1/3975* (2013.01); *H02J 7/0068* (2013.01); *H02J 7/025* (2013.01); *A61B 2560/0219* (2013.01); *A61M 2205/8206* (2013.01); *A61M 2205/8256* (2013.01)

(58) Field of Classification Search
CPC .. A61N 1/3787; A61N 1/3931; A61N 1/3968; A61N 1/3975
USPC ................. 307/154, 104; 320/103, 107, 108, 320/110–115
See application file for complete search history.

(56) References Cited

U.S. PATENT DOCUMENTS

| | | |
|---|---|---|
| 5,702,431 A | 12/1997 | Wang et al. |
| 6,169,387 B1 | 1/2001 | Kaib |
| 2004/0212344 A1 | 10/2004 | Tamura et al. |
| 2009/0163820 A1* | 6/2009 | Eerden ..................... A61B 5/00 600/481 |
| 2013/0285608 A1* | 10/2013 | Jikihara ................ H01M 10/48 320/109 |

\* cited by examiner

*Primary Examiner* — Thomas Skibinski
(74) *Attorney, Agent, or Firm* — S. Brannon Latimer

(57) ABSTRACT

A powered case is provided that includes a case, configured to hold an electroactive medical device with an integrated battery; an energizing system, configured to provide electric energy; and an energy transfer system, configured to receive energy from the energizing system; and to transfer the received energy to the integrated battery of the electroactive medical device. Further, a medical device system is provided that can include an electroactive medical device, including an integrated battery; and a powered case, including a case, configured to hold the electroactive medical device with the integrated battery; an energizing system, configured to provide electric energy; and an energy transfer system, configured to receive energy from the energizing system; and to transfer the received energy to the integrated battery of the electroactive medical device.

15 Claims, 5 Drawing Sheets

POWERED CASE FOR ELECTRO-ACTIVE MEDICAL DEVICE BATTERY MANAGEMENT

TECHNICAL FIELD

This patent document is related to electronic and opto-electronic medical devices. In more detail, this patent document is related to an electrically powered case for an electroactive medical device.

BACKGROUND

The list of electroactive medical devices is growing by the day. The list includes electroactive Intra Ocular Lenses, pacemakers, implantable drug delivery systems, neuro-stimulators, in-vivo sensors, and medical devices with rechargeable batteries.

A substantial fraction of these electroactive medical devices include an integrated, or on-board, battery to energize their on-board electronics. For implantable medical devices, rechargeable batteries are used that can energize the medical device until they are depleted, at which time they get recharged to keep the medical device operational.

Rechargeable batteries, just like all batteries, start losing their charge and thus the energy they store, once the charging is finished. There are several advantages of compensating this "self-discharging" process and keeping the charging state of the batteries of the medical devices sufficiently high after their manufacture.

One of the leading reasons is that the performance of wide classes of batteries exhibits accelerated degradation, if the self-discharging is allowed to become excessive, and the batteries' charging state is allowed to drop significantly below a lower threshold. After such an excessive self-discharge, the batteries cannot be recharged to the same energy level anymore because of irreversible electro-chemical reactions: the energy storing capacity of the batteries exhibits degradation. Such degraded batteries require recharging more frequently, and can operate only for shorter periods between recharges. Both these factors affect their functionalities negatively. Further, often the overall usable lifetime of such excessively self-discharged batteries also shrinks.

Second, a substantial time period can elapse between the manufacture of the battery of the medical device, and the implantation of the device into a patient. In this period, the self-discharging can lead to the loss of a substantial fraction of the energy stored in the battery, thus reducing the time before the battery needs recharging after implantation, possibly even rendering the implanted medical device non-operational after implantation.

For all these reasons, there is a need to compensate the self-discharging of the integrated on-board batteries of implantable electroactive medical devices between their manufacture and their implantation by keeping their charging state above a lower threshold.

Some simple solutions turn out not to be particularly workable. For example, it can be attempted to overcharge the on-board battery at the time of its fabrication, so that even after the self-discharge, its charging state remains above a lower threshold. However, such overcharging above an upper threshold can lead to a performance degradation that is comparable to the performance degradation caused by the charging state decaying below the lower threshold.

A battery manufacturer and a device manufacturer can also advise the ophthalmic surgeons to implant the devices within a short time period after the manufacture of the batteries. However, the overall distribution process is not within the control of the device manufacturer, since the sale of the device may take longer than expected, or the surgeon may store the medical device after its purchase for a period longer than desirable. Without controlling the intermediary process, the medical device manufacturer cannot provide the required guarantees about the performance of its product devices.

Finally, a periodic charging-state-monitoring protocol can be required by intermediary custodians of the medical device after its manufacture, such as a human monitor checking the charging state of the batteries manually and periodically at the intermediate stops of the distribution process, including in medical warehouses, in transit, and in hospital storage facilities. However, this approach is subject to human error, is labor intensive, and requires operating a substantial human workforce, resulting in considerable overhead costs.

For all the above reasons, new solutions are needed to compensate the self-discharging of on-board batteries of electroactive medical devices between their manufacture and the implantation of the electroactive medical device.

SUMMARY

Embodiments in this patent document address the above challenges by introducing a powered case that includes a case, configured to hold an electroactive medical device with an integrated battery; an energizing system, configured to provide electric energy; and an energy transfer system, configured to receive energy from the energizing system; and to transfer the received energy to the integrated battery of the electroactive medical device.

Further, a medical device system is provided that can include an electroactive medical device, including an integrated battery; and a powered case, including a case, configured to hold the electroactive medical device with the integrated battery; an energizing system, configured to provide electric energy; and an energy transfer system, configured to receive energy from the energizing system; and to transfer the received energy to the integrated battery of the electroactive medical device.

DETAILED DESCRIPTION

Embodiments described herein address the above needs and challenges by introducing a powered case, or packaging, to hold the electroactive medical device with an integrated battery. The powered case can involve various mechanisms to keep the integrated battery charged within an optimal charging range.

Embodiments of the powered case can be used to house electroactive Intra Ocular Lenses (TOL), or powered contact lenses. Other embodiments can be used to house other types of powered implantable medical devices. The medical devices may have a hard-to-replace battery like that of electroactive Intra Ocular Lenses (IOLs), and therefore, the functional device lifetime can be limited by the battery lifetime.

Yet other medical devices that can benefit from the combination with the present powered case include implantable drug delivery systems, neuro-stimulators, in-vivo sensors, and any device with rechargeable batteries.

An advantage to store a battery-dependent electroactive medical device in a powered case is that the battery is kept by the powered case within a desired charging range, thus keeping the lifetime of the battery close to the nominally achievable lifetime. As mentioned earlier, for example, the lifetime of the quite widely used lithium ion batteries shrinks noticeably, if they excessively self-discharge to a degree that their charging state decreases below a threshold. For this reason, storing electroactive medical devices in the here-described powered cases can extend their expected operational lifetime, sometimes by a substantial fraction. Further, for electroactive medical devices with replaceable batteries, storing them in powered cases increases the amount of time between required battery replacements. For some medical devices, disadvantageously such battery replacement may require a significant intervention, possibly involving surgery.

Figure 1:
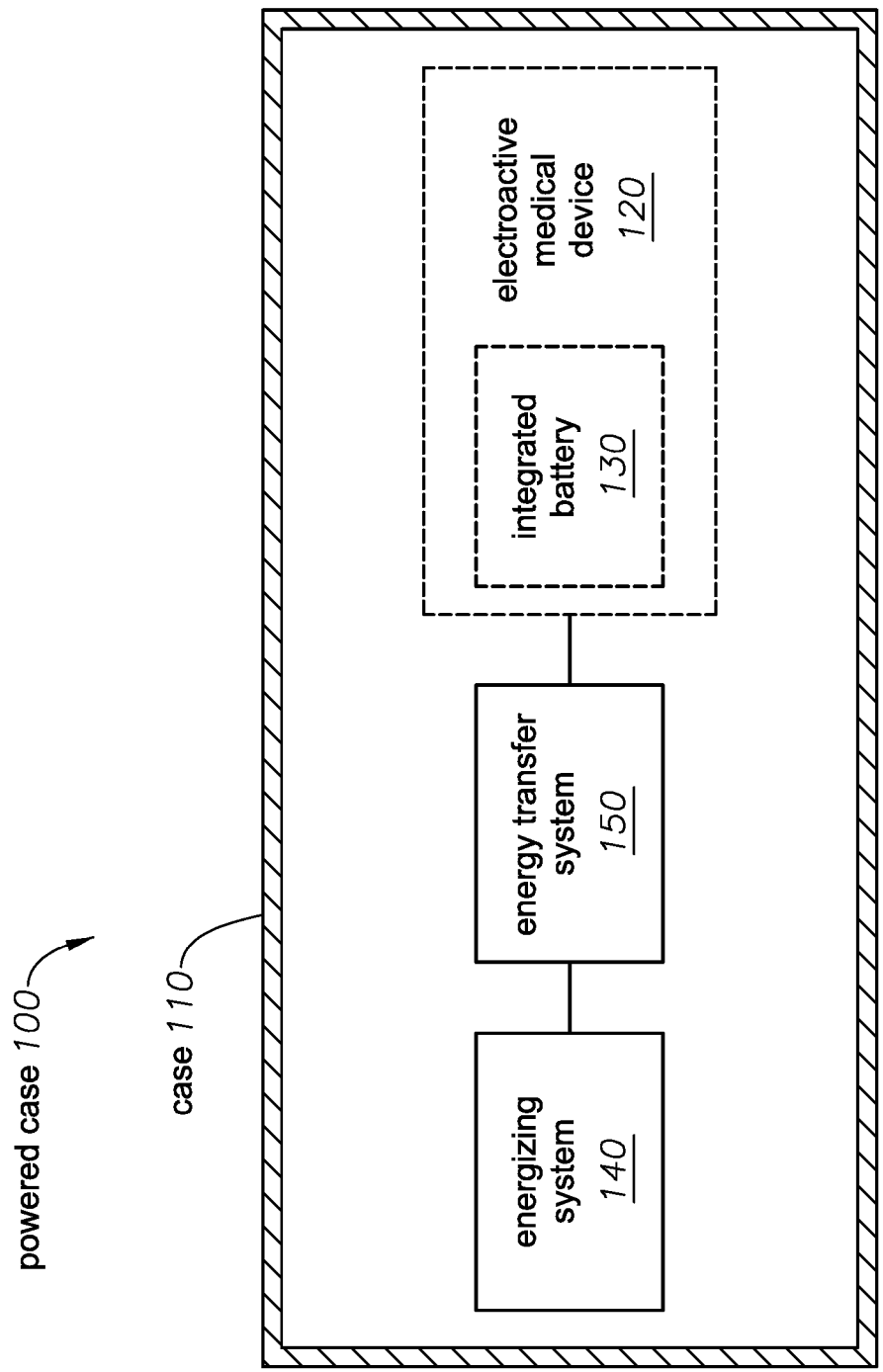
FIG. 1 illustrates a powered case 100.

FIG. 1 illustrates an embodiment of a powered case 100 that includes a case 110, configured to hold an electroactive medical device 120 with an integrated battery 130; an energizing system 140, to provide electric energy; and an energy transfer system 150, configured to receive energy from the energizing system 140 and to transfer the received energy to the integrated battery 130 of the electroactive medical device 120. In FIG. 1, the electroactive medical device 120 is indicated with dashed lines to illustrate that in these embodiments, it is not part of the powered case 100. Embodiments of the powered case 100 can be configured to be able to charge different types electroactive medical devices, or to repeatedly charge the same type of electrical device.

Figure 2:
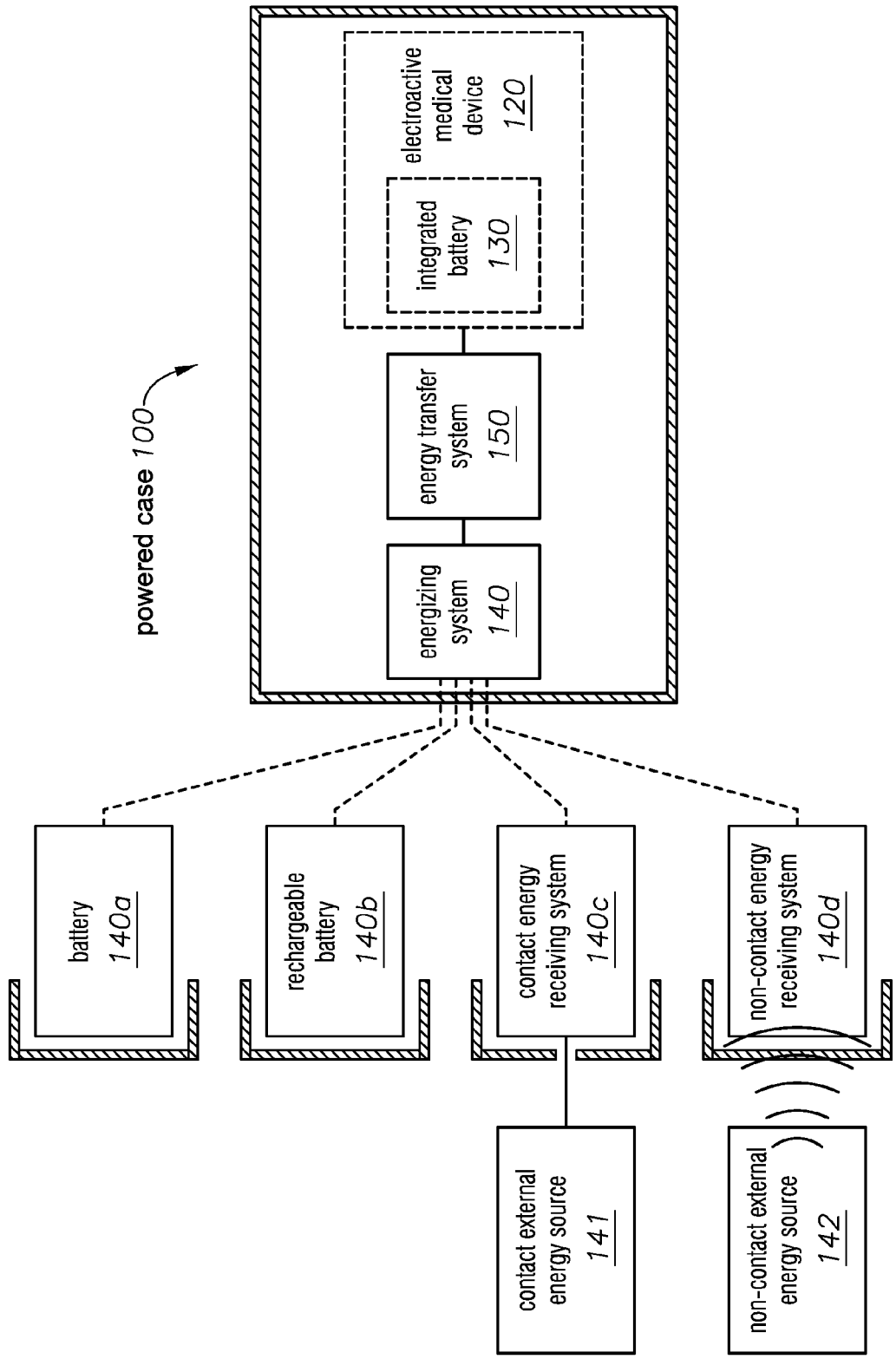
FIG. 2 illustrates embodiments of the energizing system 140.

FIG. 2 illustrates at least four embodiments of the energizing system 140. In some embodiments, the energizing system 140 can include a battery 140a. This battery 140a can be a "primary", non-rechargeable battery that may require replacements as it discharges over an extended period.

In some embodiments, the energizing system 140 can include a rechargeable battery 140b. This "secondary", rechargeable battery 140b may be recharged from an external energy source. Some embodiments of the energizing system 140 may include a charging port to recharge the rechargeable battery 140b via direct electrical contact through this charging port. Some embodiments of the energizing system 140 may include a receiving terminal of an inductive charging system to recharge the rechargeable battery 140b through non-contact induction charging.

In some embodiments, the energizing system 140 may not include batteries like 140a, or 140b. Instead, the energizing system 140 may include a contact energy receiving system 140c, configured to receive energy from a contact external energy source 141 by a contact energy transfer. A simple embodiment of such an energy receiving system 140c can include an externally accessible plug or socket, to form a direct, or contact, electrical coupling to an electrical outlet, a mains AC, or an external battery, as well as an AC/DC adapter, to step down the grid AC power to a power suitable for the energy transfer system 150, such as to a DC voltage of 6 or 12V. Other embodiments of the external energy source 141 can be selected from a wide variety of energy sources, including a fuel cell, an energy harvester, a primary cell, or another rechargeable cell.

Another, non-battery-based energizing system 140 may include a non-contact energy receiving system 140d. In some embodiments, this non-contact energy receiving system 140d can be the receiving portion of an inductive charging system, where the energy is provided by an external non-contact external energy source 142. The energy can then be transferred via a non-contact mechanism, such as induction, from the non-contact external energy source 142 to the non-contact energy receiving system 140d. In some embodiments, this transfer is facilitated by a primary coil in the non-contact energy source 142 towards a receiving secondary coil in the non-contact energy receiving system 140d.

In some embodiments of the powered case 100, a combination of more than one energizing systems 140 can be utilized.

Figure 3A:
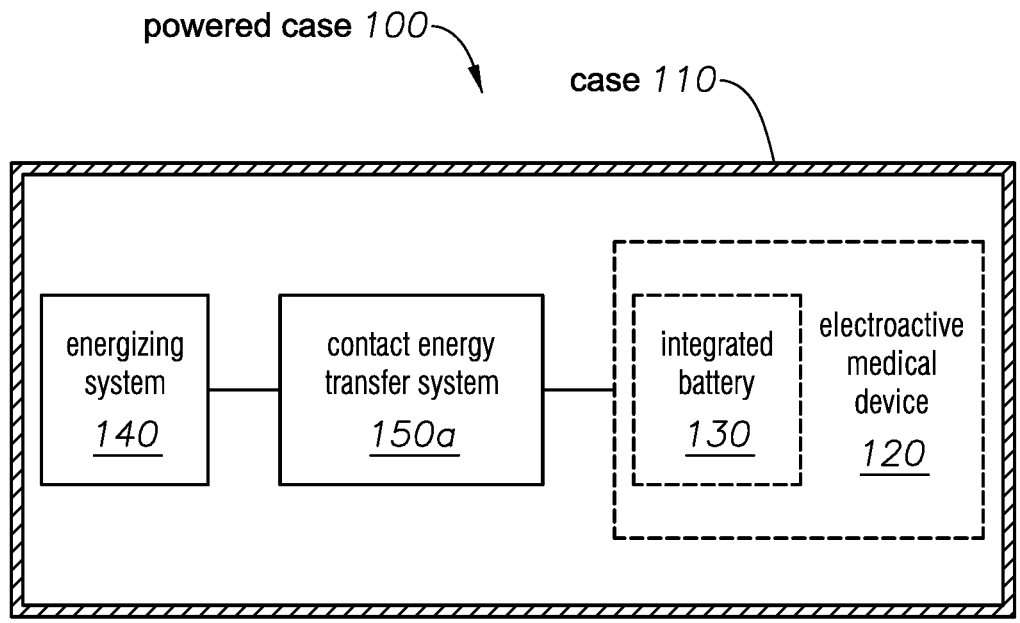
FIGS. 3A-B illustrate embodiments of the energy transfer system 150.
Figure 3B:
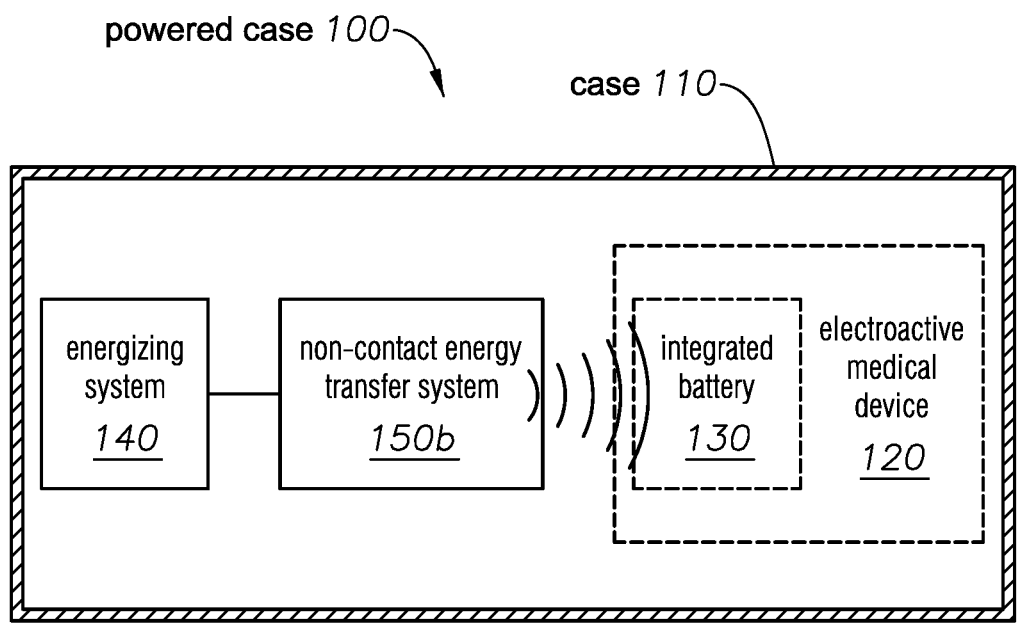

FIGS. 3A-B illustrate various embodiments of the energy transfer system 150 of the powered case 100. In the embodiment of FIG. 3A, the energy transfer system 150 can be a contact energy transfer system 150a. In a simple case, this contact energy transfer system 150a may include a plug, or socket, arrangement to make a direct, or contact, electrical coupling from the energy transfer system 150a to the integrated battery 130 of the electroactive medical device 120. The contact energy transfer system 150a may also include a regulating circuit, or a transformer, to control the transfer of energy from the energizing system 140 to the integrated battery 130.

FIG. 3B illustrates that some embodiments of the energy transfer system 150 may include a non-contact energy transfer system 150b. Such non-contact energy transfer embodiments 150b may include a primary coil of an inductive charging system, in which case the electroactive medical device 120 may include a secondary, or pickup, coil to receive the energy transferred from the primary coil.

Figure 4:
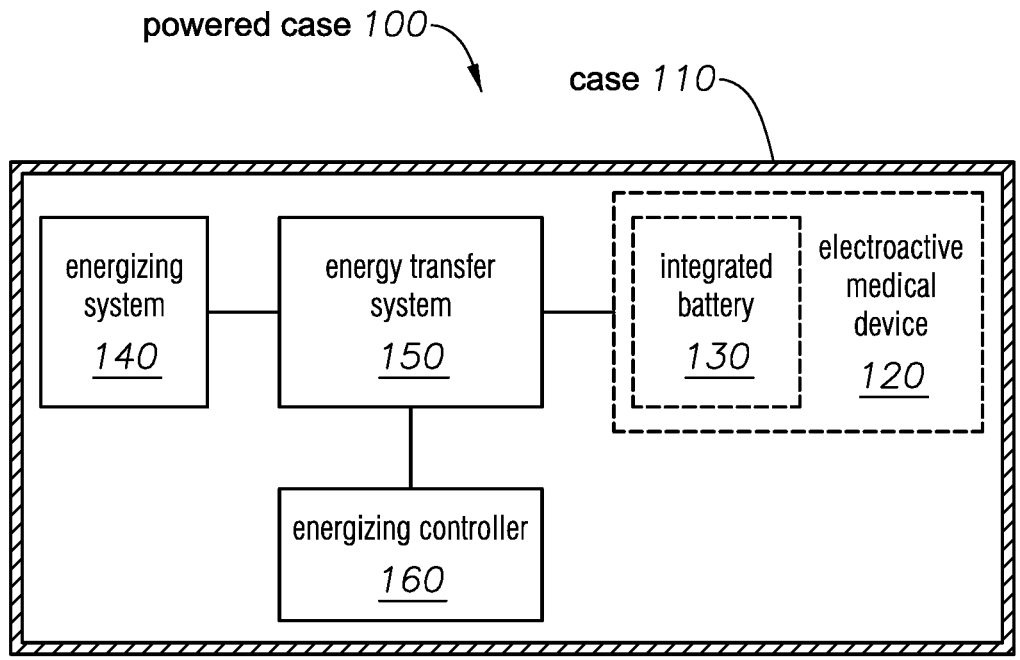
FIG. 4 illustrates a powered case 100 with an energizing controller 160.

FIG. 4 illustrates that some embodiments of the powered case 100 can include an energizing controller 160, configured to control the transfer of energy from the energizing system 140 by the energy transfer system 150 to the integrated battery 130 of the electroactive medical device 120, to at least partially compensate a discharging, or self-discharging, of the integrated battery 130.

In some embodiments, the energizing controller 160 can be configured to control the energy transfer system 150 to charge the integrated battery 130 of the electroactive medical device 120 to at least partially compensate a predetermined discharging characteristics of the integrated battery 130 according to a continuous charging protocol over one or more extended time intervals. In an embodiment, the discharging characteristics of the integrated battery 130 may be an anticipated discharging curve that was measured, or predetermined, in a laboratory setting imitating realistic circumstances. This anticipated discharging curve can be used to create, or predetermine, an energy transfer protocol that is aimed at compensating the discharging of the integrated battery 130.

In an embodiment this can be realized by predetermining the discharging curve, or discharging characteristic, of the integrated battery 130, and then calculating a compensating charging, or energizing, protocol that is anticipated to keep a charging state of the integrated battery 130 above the mentioned lower threshold, within a range from a desired operating charging state. In an informal sense, the energizing controller 160 can control the energy transfer system 150 to "top up" the integrated battery 130 with energy from the energizing system 140 to compensate the battery's anticipated discharging. In some embodiments, the energy transfer system 150 may compensate the anticipated discharging of the integrated battery 130 by carrying out a pre-determined charging protocol that is anticipated to keep the charging state of the integrated battery 130 above 80% of its nominal, or design level. In other embodiments, the charging protocol may be designed to keep the charging state of the integrated battery 130 above 90% above a nominal, or design level.

In some embodiments, the energizing controller 160 may control the energy transfer system 150 to transfer charge for the integrated battery 130 by a continuous charge "trickle" protocol. This charge transfer protocol may be continuous over intervals, but suspended between intervals.

In other embodiments, the energizing controller 160 can control the energy transfer system 150 to charge the integrated battery 130 according to an intermittent charging protocol. For example, the energy transfer system 150 may charge the integrated battery 130 in bursts that take place over short time intervals, followed by longer period of "hibernation" without charging. In other embodiments, the energy transfer system 150 may charge the integrated battery 130 at levels that vary over time. A large number of intermittent protocols can be used in various embodiments. The embodiments of the energizing controller 160, described in relation to FIG. 4, typically control energy transfers to the integrated battery 130 according to predetermined protocols, without relying on a feedback, or a direct sensing or monitoring of the charge state of the integrated battery 130.

Figure 5:
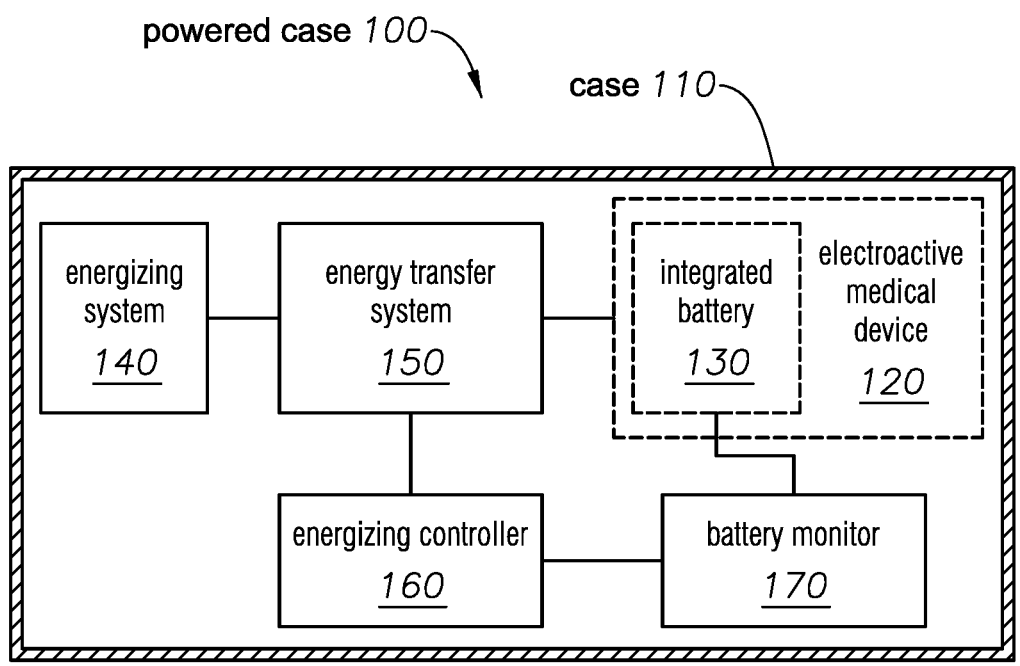
FIG. 5 illustrates a powered case 100 with a battery monitor 170.

FIG. 5 illustrates embodiments, where some type of non-predetermined information is also used by the energizing controller 160. In embodiments, the powered case 100 can include a battery monitor 170 to provide such non-predetermined information. In some embodiments, the battery monitor can be coupled to the integrated battery 130 and to the energizing controller 160. The battery monitor 170 can be designed to monitor the discharging characteristics of the integrated battery 130, and to generate a corresponding monitoring signal for the energizing controller 160. In these embodiments, the energizing controller 160 can control the energy transfer system 150 to charge the integrated battery 130 according to the monitoring signal received from the battery monitor 170.

In some embodiments, the battery monitor 170 may include a voltage sensor. When the voltage sensor senses that a voltage of the integrated battery 130 decreased below a predetermined threshold value, the battery monitor 170 may generate a monitoring signal for the energizing controller 160 to commence a charging operation by the energy transfer system 150 from the energizing system 140 to the integrated battery 130, in order to increase the voltage of the integrated battery 130 back above the threshold voltage.

Similarly to the embodiments of FIG. 4, the energizing controller 160 can be configured to control the energy transfer system 150 to charge the integrated battery 130 by an intermittent charging protocol, or by a continuous charging protocol over one or more time intervals. In some designs, the energizing controller 160 can simply provide a control signal that orders the energy transfer system 150 to execute an energy transfer protocol that is stored in the energy transfer system 150. In other designs, the energizing controller 160 may store the energizing protocol itself.

Figure 6:
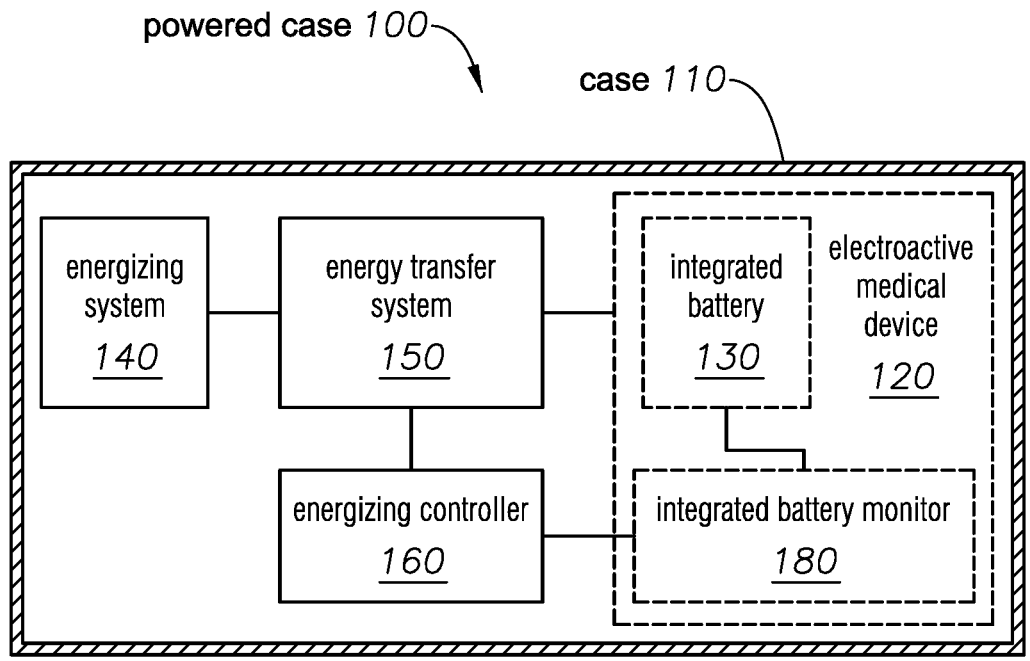
FIG. 6 illustrates a powered case with an integrated battery monitor 180.

FIG. 6 illustrates another embodiment of the powered case 100. In the embodiment of FIG. 5, the battery monitor 170 was part of the powered case 100, external to the medical device 120. In contrast, the embodiment of FIG. 6 illustrates an embodiment where the electroactive medical device 120 includes an integrated battery monitor 180. The functions of this integrated battery monitor 180 can be analogous to those of the battery monitor 170: the integrated battery monitor 180 can be configured to monitor a discharging characteristics of the integrated battery 130, and to generate a corresponding monitoring signal for the energizing controller 160.

In these embodiments, the energizing controller 160 can be configured to receive the monitoring signal from the integrated battery monitor 180, and to control the energy transfer system 150 to charge the integrated battery 130 according to the monitoring signal received from the integrated battery monitor 180. The monitoring signal can be transferred through contact signaling via a wired, direct coupling from the integrated battery monitor 180 to the energizing controller 160. In other embodiments, it can be transferred via a non-contact signal path, such as by a bluetooth system, or by any other wireless signaling technology.

As in other embodiments, the energizing controller 160 can be configured to control the energy transfer system 150 to charge the integrated battery 130 by an intermittent charging protocol, or by a continuous charging protocol over one or more time intervals.

Figure 7:
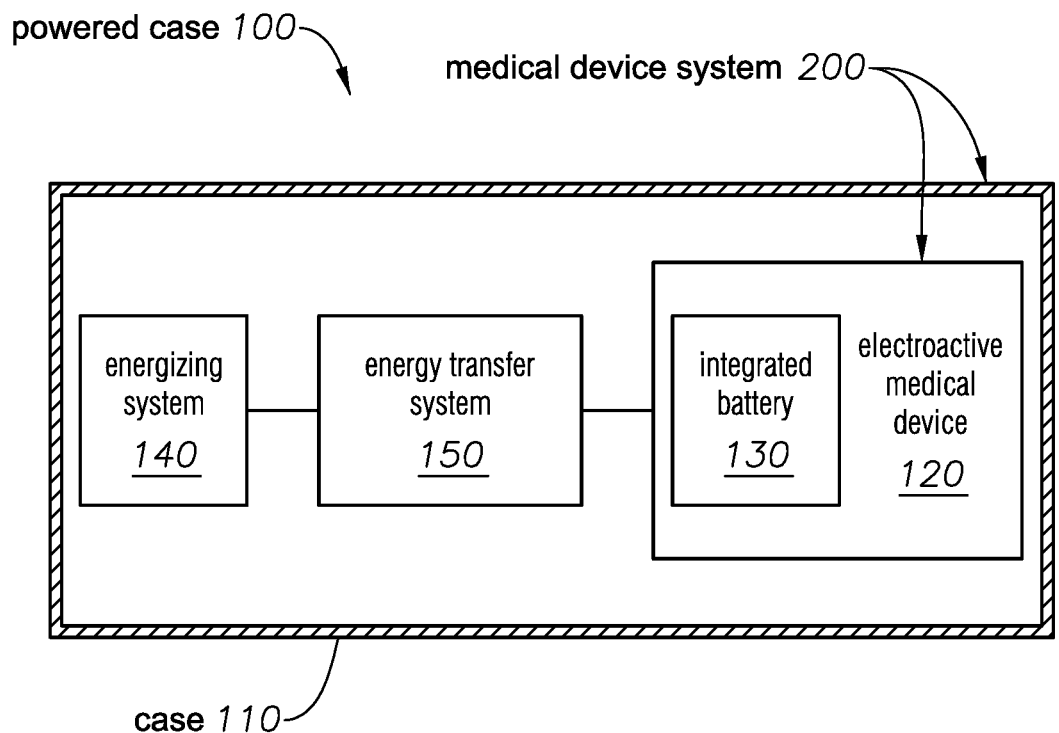
FIG. 7 illustrates a medical device system 200 with a powered case 100.

FIG. 7 illustrates an embodiment of a medical device system 200 that can include not only the powered case 100, but also the electroactive medical device 120 that can include the integrated battery 130. The powered case 100 can be analogous to any of the embodiments described in relation to FIGS. 1-6. Accordingly, it may include the case 100 to hold the electroactive medical device 120 with the integrated battery 130; the energizing system 140, configured to provide electric energy; and the energy transfer system 150, configured to receive energy from the energizing system 140; and to transfer the received energy to the integrated battery 130 of the electroactive medical device 120.

While this specification contains many specifics, these should not be construed as limitations on the scope of the invention or of what can be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features can be described above as acting in certain combinations and even initially claimed as such, one or more features from a claimed combination can in some cases be excised from the combination, and the claimed combination can be directed to a subcombination or variation of a subcombination.

The invention claimed is:
1. A powered medical device storage case, comprising:
a case, configured to hold an implantable electroactive medical device with an integrated battery after manu- facture of the implantable electroactive medical device and before implantation of the implantable electroactive medical device;
an energizing system, configured to provide electric energy; and
an energy transfer system, configured
to receive energy from the energizing system; and
to transfer the received energy to the integrated battery of the implantable electroactive medical device; and
an energizing controller, configured to control the transfer of energy from the energizing system by the energy transfer system to the integrated battery of the implantable electroactive medical device to at least partially compensate a discharging of the integrated battery after manufacture and before implantation of the implantable electroactive medical device.

2. The powered case of claim 1, the energizing system comprising:
a battery.

3. The powered case of claim 1, the energizing system comprising:
a rechargeable battery, configured to be recharged from an external energy source.

4. The powered case of claim 1, the energizing system comprising:
an energy receiving system, configured to receive energy from an external energy source by at least one of a contact and a non-contact energy transfer.

5. The powered case of claim 1, wherein:
the energy transfer system is at least one of
a contact energy transfer system, and
a non-contact energy transfer system.

6. The powered case of claim 1, wherein:
the energizing controller is configured to control the energy transfer system to charge the integrated battery of the electroactive medical device to at least partially compensate a predetermined discharging characteristics of the integrated battery according to a continuous charging protocol over one or more extended time intervals.

7. The powered case of claim 1, wherein:
the energizing controller is configured to control the energy transfer system to charge the integrated battery of the electroactive medical device to at least partially compensate a predetermined discharging characteristics of the integrated battery according to an intermittent charging protocol.

8. The powered case of claim 1, comprising:
a battery monitor, coupled to the integrated battery and to the energizing controller, configured
to monitor a discharging characteristics of the integrated battery of the electroactive medical device, and
to generate a corresponding monitoring signal for the energizing controller.

9. The powered case of claim 8, wherein:
the energizing controller is configured to control the energy transfer system to charge the integrated battery of the electroactive medical device according to the monitoring signal received from the battery monitor.

10. The powered case of claim 9, wherein:
the energizing controller is configured to control the energy transfer system to charge the integrated battery of the electroactive medical device by at least one of
an intermittent charging protocol; and
a continuous charging protocol over one or more time intervals.

11. The powered case of claim 1, wherein:
the electroactive medical device includes an integrated battery monitor, configured to monitor a discharging characteristics of the integrated battery of the electroactive medical device, and
to generate a corresponding monitoring signal for the energizing controller; and
the energizing controller is configured
to receive the monitoring signal from the integrated battery monitor, and
to control the energy transfer system to charge the integrated battery of the electroactive medical device according to the monitoring signal received from the integrated battery monitor.

12. The powered case of claim 11, wherein:
the energizing controller is configured to receive the monitoring signal from the integrated battery monitor by at least one of
a contact signaling, and
a non-contact signaling.

13. The powered case of claim 11, wherein:
the energizing controller is configured to control the energy transfer system to charge the integrated battery of the electroactive medical device by at least one of
an intermittent charging protocol; and
a continuous charging protocol over one or more time intervals.

14. A medical device system, comprising:
an implantable electroactive medical device, including an integrated battery; and
a powered medical device storage case, including
a case, configured to hold the electroactive medical device with the integrated battery after manufacture of the electroactive medical device and before implantation of the electroactive medical device;
an energizing system, configured to provide electric energy; and
an energy transfer system, configured
to receive energy from the energizing system; and
to transfer the received energy to the integrated battery of the electroactive medical device; and
an energizing controller, configured to control the transfer of energy from the energizing system by the energy transfer system to the integrated battery of the implantable electroactive medical device to at least partially compensate a discharging of the integrated battery after manufacture and before implantation of the implantable electroactive medical device.

15. The medical device system of claim 14, wherein:
the implantable electroactive medical device is one of an electroactive Intra Ocular Lens, a pacemaker, an implantable drug delivery system, a neuro-stimulator, an in-vivo sensor, and a medical device with a rechargeable battery.

* * * * *